US006821532B2

(12) United States Patent
Randhava et al.

(10) Patent No.: US 6,821,532 B2
(45) Date of Patent: Nov. 23, 2004

(54) METHODS AND COMPOSITIONS FOR THE TREATMENT OF BENIGN PROSTATIC HYPERTROPHY

(75) Inventors: Sikander Randhava, Evanston, IL (US); Surjit Randhava, Evanston, IL (US); Sarabjit Randhava, Evanston, IL (US)

(73) Assignee: Unitel Technologies, Inc., Mt. Prospect, IL (US)

( * ) Notice: Subject to any disclaimer, the term of this patent is extended or adjusted under 35 U.S.C. 154(b) by 0 days.

(21) Appl. No.: 09/992,433

(22) Filed: Nov. 16, 2001

(65) Prior Publication Data

US 2003/0096024 A1 May 22, 2003

(51) Int. Cl.[7] .......................... A61K 35/78; A61K 9/52; A61K 9/22
(52) U.S. Cl. .................. 424/727; 424/457; 424/468; 424/725; 424/747; 514/963; 514/964
(58) Field of Search ................. 424/457, 468, 424/725, 727, 747; 514/963, 964

(56) References Cited

U.S. PATENT DOCUMENTS

| 4,140,255 | A |   | 2/1979  | Weiler ..................... 224/42.06 |
| 4,248,857 | A |   | 2/1981  | DeNeale et al. ............... 424/21 |
| 4,259,314 | A |   | 3/1981  | Lowey ......................... 424/19 |
| 4,309,404 | A |   | 1/1982  | DeNeale et al. ............... 424/21 |
| 4,610,870 | A |   | 9/1986  | Jain et al. .................... 424/19 |
| 4,615,697 | A |   | 10/1986 | Robinson .................... 604/890 |
| 4,695,467 | A |   | 9/1987  | Uemura et al. .............. 424/502 |
| 4,725,593 | A |   | 2/1988  | Davis .......................... 514/210 |
| 5,102,666 | A | * | 4/1992  | Acharya |
| 5,133,974 | A |   | 7/1992  | Paradissis et al. .......... 424/480 |
| 5,225,212 | A |   | 7/1993  | Martin et al. ................ 424/450 |
| 5,415,878 | A |   | 5/1995  | Newton et al. .............. 424/722 |
| 5,474,768 | A |   | 12/1995 | Robinson ................. 424/78.31 |
| 5,543,146 | A |   | 8/1996  | Perez ....................... 424/195.1 |
| 5,783,212 | A |   | 7/1998  | Fassihi et al. ............... 424/472 |
| 5,876,744 | A |   | 3/1999  | Della Valle et al. ......... 424/434 |
| 6,019,976 | A |   | 2/2000  | Bryant .................... 424/195.1 |
| 6,039,950 | A |   | 3/2000  | Khwaja et al. ........... 424/195.1 |
| 6,124,477 | A |   | 9/2000  | Harris ......................... 594/264 |
| 6,197,309 | B1 |  | 3/2001  | Wheeler .................. 424/195.1 |
| 6,200,573 | B1 | * | 3/2001 | Locke |
| 6,207,694 | B1 | * | 3/2001 | Murad |
| 6,231,866 | B1 | * | 5/2001 | Mann |
| 6,245,357 | B1 |  | 6/2001  | Edgren et al. .............. 424/473 |
| 6,440,467 | B2 | * | 8/2002 | Mann |
| 6,479,545 | B1 | * | 11/2002 | Levinson et al. |
| 2001/0008638 | A1 | * | 7/2001 | Wilding |
| 2002/0071868 | A1 | * | 6/2002 | Jia |
| 2002/0103139 | A1 | * | 8/2002 | Weisspapir et al. |

FOREIGN PATENT DOCUMENTS

EP    0 974 345 A2    1/2000    ............ A61K/9/48

OTHER PUBLICATIONS

Weisser et al., *Prostate*, 28, 300–306, 1996.
Carraro et al., *Prostate*, 29, 231–240, 1996.
Inter–Cal Corporation Brochure "Palmettx—Solvent–Free, Standardized Extract of Saw Palmetto".
Lehr et al., *J. Pharm. Pharmacal.* 44:(1992) pp. 402–407.

* cited by examiner

Primary Examiner—Christopher R. Tate
(74) Attorney, Agent, or Firm—Gilberto M. Villacorta; Dawn C. Hayes; Katten Muchin Zavis Rosenman

(57) ABSTRACT

This invention relates to a composition for use in treating benign prostatic hyperplasia including a saw palmetto extract provided in an oral controlled release formulation which allows release of active ingredients in the intestinal tract and which allows the maintenance of therapeutic levels of active agents in the bloodstream for prolonged periods of time. This invention also relates to a composition for improving the efficacy of a saw palmetto extract, a method of treating benign prostatic hypertrophy, and a method of improving the efficacy of a saw palmetto extract treatment.

19 Claims, No Drawings

METHODS AND COMPOSITIONS FOR THE TREATMENT OF BENIGN PROSTATIC HYPERTROPHY

BACKGROUND OF THE INVENTION

1. Field of the Invention

This invention relates to a composition for use in treating benign prostatic hyperplasia, which comprises saw palmetto extract contained in a controlled delivery system. The composition is preferably administered orally, uses a controlled delivery system to provide a targeted, extended release of the saw palmetto extract into the bloodstream.

2. Related Art

Many men over the age of fifty commonly experience a condition known as benign prostatic hyperplasia, or BPH. BPH affects as much as 40% of the male population over the age of seventy. The condition is commonly recognized as a swelling of the prostate gland. This problem gradually manifests itself in the form of a) frequent urination, b) small discharge volumes and "dribbling", and c) unsatisfying bladder evacuations. Waking up to urinate once or more each night is a typical sign of this problem. BPH is a chronic condition that tends to gradually worsen with age.

The increased incidence of BPH in older men may be due to the fact that as men age, testosterone levels tend to decline and estrogen levels rise. In the process, testosterone metabolism takes a different pathway, and testosterone is converted to dihydrotestosterone (DHT), a potent male hormone that causes prostate enlargement. The actions of DHT can be limited by restricting the enzymatic production of DHT from testosterone and/or blocking the direct pharmacological action of DHT at the receptor level. Current therapies for BPH focus on limiting the actions of DHT, and include: pharmaceutical intervention with 5-$\alpha$-reductase inhibitors such as finasteride (Proscar®); pharmacological intervention with $\alpha$-adrenergic blockers, such as terazosin HCl (Hytrin®), and doxazosin mesylate (Cardura®); prostatectomy; and administration of saw palmetto extract.

Extract of the saw palmetto berry (*Serenoa repens*) has been demonstrated to be effective in treating the symptoms of BPH in numerous clinical trials, including a number of double-blind studies. For example, a meta-analysis of existing clinical evidence for the efficacy and safety of the use of saw palmetto extract to treat BPH was published by Witt et al., *JAMA* (1999), 18:1604–1609. This analysis concludes that saw palmetto extract is effective in treating BPH, as compared with Proscar®.

Saw palmetto extracts have been used in various products intended to treat BPH. For example, in U.S. Pat. No. 5,543,146, a composition for dietary supplements including pumpkin seed, extracts of saw palmetto, and various other components is disclosed. This composition is used as a dietary supplement for alleviating the symptoms associated with enlargement of the prostate gland.

In U.S. Pat. No. 6,200,573, which relates to a method for managing BPH, a combination therapy of an $\alpha$-adrenergic antagonist such as terazosin and a phyto-therapeutic agent such as saw palmetto extract is disclosed. The active ingredients may be administered in combination with diluents and other carriers, for oral or parental administration, or may be delivered by any conventional delivery system. It is also disclosed that the active ingredients may also be formulated into once-a-day or longer sustained release compositions, although no guidance is given in this regard.

U.S. Pat. No. 6,039,950 relates to a method of making medicinally-useful saw palmetto materials in pharmaceutically acceptable forms. It discloses compositional and activity fingerprints for use in processing saw palmetto materials to produce compositions suitable for use in clinical or veterinary settings to treat various conditions. The method involves measuring the bioactivity of a sample of saw palmetto extract using an androgen receptor binding inhibition assay.

U.S. Pat. No. 6,197,309 relates to a composition for preventing or improving disorders of the prostate gland. The composition preferably includes therapeutically effective amounts of vitamin C, vitamin B-6, vitamin E, zinc, glycine, L-alanine, glutamic acid, saw palmetto extract, Pygeum extract, pumpkin seed, stinging nettle, Echinacea, garlic, ginkgo biloba, and selenium.

Finally, U.S. Pat. No. 6,019,976 relates to therapeutic formulations containing saw palmetto extract, vitamin B-6, vitamin B-3, zinc, and L-arginine. The formulations are used to treat male pattern baldness by topical application to the hair. The formulations may also be provided in the form of a drink, or in a capsule formed of gelatin and glycerin.

Other compositions have been focused on treating smooth muscle spasms, such as those that occur in the bladder, prostate, and urethra, including the compositions disclosed in U.S. Pat. No. 4,725,593. Such compositions may be administered orally, by intravenous injection, or by topical application.

None of the methods or compositions discussed above address treating benign prostatic hyperplasia by administering saw palmetto extract in a controlled delivery vehicle for extended, targeted release of the extract in the small intestine. Further, none of the methods or compositions discussed above address a method of improving the delivery of saw palmetto extract by providing the extract in the form of an oral administration vehicle comprising a controlled release system.

SUMMARY OF THE INVENTION

This invention relates to a method for improving the efficacy and convenience of oral saw palmetto therapy in the treatment of benign prostatic hyperplasia, or BPH, through the use of a controlled release formulation. The controlled release formulation allows the targeted release of the extract in a specific part or parts of the digestive system, and the extended release of the extract over the course of digestion. The targeted release is designed to deliver the active agent, extract of the saw palmetto berry (i.e., especially the phytosterols contained therein), to the portions of the digestive tract most suited for its absorption. The extended release is also designed to deliver the extract over a period of time, determined by routine methods, to be of the optimum length for this type of therapy. The controlled release saw palmetto extract composition of this invention improves the effectiveness of saw palmetto therapy for BPH by optimizing the absorption of the extract within the digestive tract, maintaining a therapeutic level of the active agent in the bloodstream for a sufficient length of time so as to reduce the dosages and the frequency (i.e., preferably once a day). The composition of this invention also improves the efficiency of saw palmetto therapy by combining the saw palmetto extract with one or more additional antispasmodic agents.

The methods and compositions of this invention address the need in the art for a more effective and convenient BPH treatment, as set forth above. More specifically, one aspect of this invention provides a composition for use in treating benign prostatic hyperplasia and comprises a saw palmetto extract provided in a controlled release oral delivery formulation, which comprises, for example, a coating formed from a material impervious to acidic conditions in the stomach that is soluble in the duodenum and small intestine.

According to another aspect of this invention, a composition for improving the effectiveness of saw palmetto extract therapy comprises a saw palmetto extract provided in a controlled release oral formulation, which comprises a coating formed from a material impervious to acidic conditions in the stomach that is soluble in the duodenum and small intestine.

According to an additional aspect of this invention, a composition for improving the efficacy of saw palmetto extracts comprises an effective amount of a saw palmetto extract, and one or more antispasmodic compounds (compounds which reduce smooth muscle contractions) selected from the group consisting but not limited to extracts or tinctures of Belladonna alkaloid, Choleus Forskholi, European Goldenrod, Peppermint, and Passion Fruit seed.

A preferred composition of the present invention comprises a two-part hard shell capsule that encases a matrix holding from about 100 mg to about 1 g of saw palmetto extract, and more preferably about 320 mg of the extract.

According to a further aspect of this invention, an improvement in an orally-administered controlled-release composition comprising saw palmetto extract comprises a compound that minimizes smooth muscle contractions, the controlled release system being selected from the group consisting of microencapsulation in coatings of variable thickness, each with a different dissolution pattern; encapsulation in a material matrix that dissolves slowly in the neutral environment of the duodenum and small intestine; and binding with bioadhesives that adhere to the wall of the small intestine.

According to yet another aspect of this invention, a method of treating benign prostatic hyperplasia comprises the step of administering a therapeutically effective amount of a saw palmetto extract provided in a controlled release oral formulation that includes a coating formed from a material impervious to acidic conditions in the stomach, but which is soluble in the duodenum and small intestine.

According to an additional aspect of this invention, a method of improving the efficacy of saw palmetto extract treatment comprises the steps of providing a therapeutically effective amount of a saw palmetto extract in an oral formulation, and encapsulating the saw palmetto extract in a coating formed from a material impervious to acidic conditions in the stomach that is soluble in the duodenum and small intestine.

According to a further aspect of this invention, a method for improving the efficacy of saw palmetto extract treatment comprises the steps of providing a therapeutically effective amount of a saw palmetto extract, and further providing one or more antispasmodic compounds selected from the group consisting of extracts or tinctures of Belladonna alkaloid, Choleus Forskholi, European Goldenrod, Peppermint, and Passion Fruit seed.

It will be apparent to those skilled in the art that only the preferred embodiments have been described by way of exemplification, and that there are various modifications which fall within the scope of this invention. These and other aspects of the invention will be discussed in greater detail below.

DETAILED DESCRIPTION OF THE PREFERRED EMBODIMENTS

While the present invention will be described primarily with respect to a method and composition for treating BPH, and improving the delivery of saw palmetto extract, it is to be understood that the features thereof will find applicability to other areas, such as the treatment of other disorders related to increased levels of DHT, such as male pattern baldness. The term "benign prostatic hyperplasia" or "BPH" as used herein is meant to refer to the condition characterized by swelling of the prostate gland, and the accompanying frequent urination and small discharge volumes. The term "saw palmetto extract" as used herein is meant to refer to the extract of the saw palmetto plant (*Serenoa repens*) in the form of an oil, a water-soluble concentrate, or an alcohol-soluble concentrate of that plant. The terms "extended release", "targeted release", and "controlled release" as used herein are meant to refer to a delivery system or formulation for oral delivery, characterized, for example, by a coating used to control the rate and/or location of the release of the active ingredients of the oral formulation, or by an enteric coating.

The saw palmetto extract according to this invention is preferably in the form of an oil, is preferably derived from the saw palmetto berry, and may be metabolized much like any other fat or oil. Is likely that the triglycerides that make up the oil are digested by gastric and intestinal lipases and bile acids into free fatty acids and monoglycerides, which are a suitable form for absorption. These monoglycerides form micelles that further solubilize the fatty acids, and the micelles are absorbed by the mucosal cells of the small intestine. However, fatty acids are not likely to be the therapeutically active components in saw palmetto extract's treatment of BPH. The compounds in saw palmetto extract hypothesized to mediate BPH therapy are the phytosterols, or plant hormones. The phytosterols may also use lipids as a carrier, and this may be the means by which they are absorbed by the mucosal cells of the small intestine.

Through use of extended release technologies, the present invention allows the maintenance of an extended release of the active ingredients in the duodenum and small intestine for between 3 and 24 hours. Such technologies allow extension of the theoretical ceiling for delivery of the active ingredient beyond the typical transit time through this region of the gastrointestinal tract.

While not intending the invention to be limited by specific mechanisms, the pharmacological effect of saw palmetto extract is hypothesized to occur by one or more of the following four mechanisms of action, which are presented by way of illustration, and not limitation.

1. Blockage of the Enzyme 5-α-reductase

This enzyme governs the conversion of testosterone to DHT, which is a potent hormone that causes the prostate to increase in mass. In BPH, the increased tissue mass is benign; however, the urological complications are severe enough that intervention is usually eventually required. DHT is also known to be involved in male pattern baldness. In fact, finasteride (Propecia®) a 5-α-reductase inhibitor, is prescribed for this condition. DHT has also been implicated in the dermatological hormone-related problems of adolescent acne. It appears that phytosterols may block the binding of testosterone to 5-α-reductase by competing for the same binding site on the 5-α-reductase enzyme.

2. Direct Blockage of DHT Receptors

In addition to inhibiting DHT synthesis, saw palmetto extract appears to block the androgen receptors to which DHT binds and through which it exerts its biological effects, including prostate enlargement. Finasteride has not been demonstrated to have this direct and independent action on androgen receptors.

3. Blockage of Adrenergic Receptors

Evidence suggests that saw palmetto extract also blocks α-adrenergic receptors, which are well-recognized pharmacological targets for the treatment of BPH. This mechanism provides relief to BPH patients via smooth muscle relaxation in the bladder neck, prostate capsule, and prostatic urethra, resulting in a number of beneficial urological effects. However, the use of selective α-adrenergic pharmaceutically pure compounds, such as Terazosin®, which possesses a high side effect profile, is limited by unwanted cardiovascular effects.

4. Anti-inflammatory Activity

Increasing evidence suggests that phytosterols have anti-inflammatory properties with respect to the prostate gland. Extract of saw palmetto has been shown to inhibit cyclooxygenase and 5-lipoxygenase, enzymes which are involved in the inflammatory process. Beneficial effects of phytosterols include the normalization of capillary permeability. This provide clinical benefits to BPH patients because the prostate often becomes inflamed as it enlarges.

This invention relates to an orally delivered capsule, pill, or other oral dosage form that improves the efficacy of saw palmetto treatment for BPH by controlling and targeting the release of the active ingredient in the receiving membranes of the small intestine, and continuing an extended release of the extract over the course of its travel through the duodenum and small intestine. The targeted release of the extract into the small intestine is achieved by coating the pill or capsule with a material impervious to the acidic environment of the stomach, which has a pH of approximately 2 to 3 and which provides a controlled extended release of the extract and which avoids the spike and collapse phenomenon seen with standard gel cap or tablet release. The coating of the pill should also be soluble in the more neutral environment of the duodenum and small intestine. This controlled release prevents the active ingredient from being degraded due to exposure to the highly acidic environment of the stomach and allows the maintenance of therapeutic blood levels of the active ingredients over extended periods of time. Such degradation may include, but is not limited to: cleaving of the phytosterols from their fatty acid carriers, and alteration or degradation of the phytosterols themselves.

The extended release of the extract over the course of its travel through the duodenum and small intestine can be achieved by any of a number of slow dissolution technologies. These include, but are not limited to: microencapsulation of the extract in coatings of variable thickness, each with a different dissolution pattern; encapsulation of the extract within a material matrix that dissolves slowly in the neutral environment of the duodenum and small intestine; and binding of the extract with bioadhesives which adhere to the wall of the small intestine, for the purpose of providing extended, targeted release. Controlled release systems are described, for example, in U.S. Pat. Nos. 6,124,477; 5,783,212; 5,415,878; 5,225,212; 5,133,974; 4,695,467; 4,610,870; 4,259,314; 4,309,404; 4,248,857; and 4,140,255, all of which are incorporated herein by reference in their entirety.

A preferred capsule coating for use in the compositions of this invention is described in European Patent EP 0 974 345, to MW Encap Ltd. (incorporated herein by reference). This coating comprises a suitable capsule material, such as gelatin or hydroxypropylmethylcellulose (HPMC), to which a solute, such as propan-1-ol, propan-2-ol, or another alcohol, is added to elevate the thermal gelation temperature of the capsule material. A plasticizer such as propylene glycol may also be added. A gelling agent comprising one or more gums (e.g., gellan gum) may also be used in the coating. Finally, a hydrating agent may be included to aid in solubilizing the gum, and the hydrating agent may optionally be sodium citrate. The coating is prepared by heating a solution of the capsule material and the solute, and optionally a plasticizer. The gelling agent and hydrating agent are heated separately. When both heated solutions reach the desired temperature, they are thoroughly mixed to form the coating.

The extended release system according to this invention maximizes the release time of the extract in the small intestine. This has the effect of maintaining therapeutic levels of the active ingredient in the blood for an extended length of time, eliminating the spike and collapse pattern associated with less sophisticated medication systems that release their active ingredients more rapidly into the digestive system. The extended release system preferably allows a medication schedule of one oral dosage per day. The currently recommended medication schedule for standard saw palmetto extract compositions for the treatment of BPH is 160 milligrams (mg) of the extract twice a day: once in the morning, once in the evening. It is well-recognized that a once-a-day medication schedule is far more likely to be followed by patients, and therefore is more likely to be effective. Further, the saw palmetto extract composition with an extended release system according to this invention maintains a more even therapeutic level of the active ingredient in the bloodstream. Therefore, the preferred doses of the compositions of this invention include from about 50 mg to about 1 g of saw palmetto extract, and most preferably 320 mg.

Oral preparations of the saw palmetto extract useful in the practice of this invention may be prepared as a plant oil, or an aqueous or organic extract of the whole plant or a selected part of the plant. According to one aspect of this invention, the extract is preferably derived from the saw palmetto berry. The compositions of this invention can also utilize saw palmetto that has been processed in whole or in part to form a powder. Extracts of the plant material (especially an oil) are presently preferred; however, powdered plant materials are also well-suited for oral applications where the drug is administered in solid form, e.g., tablets or capsules. In a preferred embodiment of the present invention, the saw palmetto extract is a solvent-free high purity, high potency extract prepared using a supercritical carbon dioxide extraction process. Such extraction processes are well known in the art.

In addition to the saw palmetto extract, which contains the active ingredients, the oral preparations of this invention may also contain appropriate tablet additives, including: diluents such as calcium carbonate, magnesium carbonate, dicalcium phosphate or mixtures thereof; binders such as hydroxypropyl-methylcellulose, hydroxypropylcellulose, polyvinylpyrrolidone, pregelatinized starch or gum acacia or mixtures thereof; disintegrants such as cross-linked polyvinylpyrrolidone, sodium starch glycolate, croscarmellose sodium or mixtures thereof; lubricants, such as magnesium stearate or stearic acid, glidants; or flow aids, such as colloidal silica, talc or starch; and stabilizers, such as desiccating amorphous silica, coloring agents, and flavors.

The oral formulations according to the present invention are controlled or extended release formulations. The controlled release system or extended release formulation according to this invention is believed to control the absorption of the phytosterols present in the saw palmetto extract by coating it with a substance that retards release of the drug at certain pH values, while promoting disintegration and/or leaching of the drug at other pH values. The coating is designed to prevent premature disintegration of the capsule, tablet, or other oral dosage form in the acidic environment of the stomach, and to promote release of the drug in the intestine. A suitable controlled release capsule coating is one which will dissolve upon contacting intestinal fluids at higher pH levels (pH greater than 4.5), such as those found within the duodenum and small intestine. The pH of the small intestine gradually increases from about 4.5 to about 6.5 in the duodenal bulb, to about 7.2 in the distal portions of the small intestine (ileum). In order to provide predictable dissolution corresponding to the small intestine transit time of about 3 hours to about 24 hours and permit reproducible release therein, the coating should begin to dissolve within the pH range of the duodenum and continue to dissolve at the pH range within the small intestine. Therefore, the amount of controlled release capsule coating should be such that it is substantially dissolved during the desired transit time within the duodenum and small intestine. It should be noted that little absorption of the phytosterols of the saw palmetto extract can occur after the composition enters the large intestine. As described above, a preferred controlled-release capsule formulation is set forth in European Patent EP 0 974 345, which is incorporated herein by reference.

A preferred composition according to the present invention comprises a two-part hard shell capsule that encases a matrix holding from about 50 mg to about 1 g saw palmetto extract. A more preferred composition comprises a two part hard shell capsule encasing a matrix holding about 320 mg of saw palmetto extract.

Enteric coatings may be provided as part of the oral dosage formulation. The enteric coating may be an essentially conventional coating material known for enteric coating, for example, enteric polymers such as cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, etc. These may be used either alone or in combination, or together with other polymers than those mentioned above. The enteric coating may also include insoluble substances which are neither decomposed nor solubilized in living bodies, for example, alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, 1,2,3,4-diepoxybutane, etc. The enteric coating may also include starch and/or dextrin. The enteric coating may also include an anti-tack agent such as talc, silica, or glyceryl monostearate. The enteric coating can also contain other ingredients such as surfactants, pigments, and fillers. The enteric coating may be found on the oral formulations of this invention and may be formed as a single layer, or as multiple layers. If the coating includes multiple layers, then compositions of the layers may be the same or different, and may be of the same or varying thicknesses. The controlled release system may also include providing an agent that acts to bind the saw palmetto extract to the walls of the small intestine.

According to an additional aspect of this invention, the controlled-release saw palmetto extract formulation may be combined with an additional compound useful in treating spasms in smooth muscle fibers. Such a compound would aid in treating BPH symptoms by minimizing bladder and urethral contractions that cause sudden urges to urinate. Antispasmodic compounds useful in minimizing such smooth muscle contractions include, but are not limited to: extracts or tinctures of Belladonna alkaloid, Choleus Forskholi, European Goldenrod, Peppermint, and Passion Fruit seed.

It is envisioned that additional compounds may optionally be administered along with the compositions of this invention, either by including the compounds in the composition, or by co-administering the compound. Such compounds may include NSAIDS (e.g., ibuprofen, naproxin sodium), COX-2 inhibitors (e.g., celecoxib, refecoxib), and others.

The compositions of the present invention may optionally contain a bioadhesive which allows adherence of the compositions to the intestinal mucosal thereby providing an additional means by which to control the extended release characteristics of the compositions. Such bioadhesives include but are not limited to polycarbophil containing bioadhesives and others such as those described in U.S. Pat. Nos. 5,876,744; 5,474,768, and 4,615,697 all of which are incorporated herein by reference in their entirety.

The following examples are intended to be illustrative of the invention and are not intended to limit the invention as set out in the appended claims.

Example 1 describes an exemplary extended release formulation of saw palmetto extract. Example 2 describes an exemplary formulation of saw palmetto extract in combination with an antispasmodic compound.

EXAMPLE 1

Extended Release Formulation of Saw Palmetto Extract

A preferred extended release formulation of the present invention comprises a two-part hard shell capsule that encases a matrix (preferably a fatty matrix) that in turn comprises about 50 mg to about 1 g of saw palmetto extract. Other suitable matrices are well known in the art. Preferably, the formulation comprises about 320 mg of extract. Preferably, the shell comprises a material free of animal components. A preferred saw palmetto extract is prepared by an extraction process that is free of organic solvents and which provide a high-purity, high potency saw palmetto oil. Such an extract may be prepared using a high pressure, supercritical carbon dioxide extraction process, by methods well known in the art.

The capsule is formed from a material such as gelatin or hydroxypropylmethyl cellulose (HPMC), to which a solute, such as propan-1-ol, propan-2-ol, or another alcohol, is added to elevate the thermal gelation temperature of the capsule material. A plasticizer such as propylene glycol may also be added. A gelling agent comprising one or more gums (e.g. gellan gum) may also be used in the coating. Finally, a hydrating agent may be included to aid in solubilizing the gum, and the hydrating agent may optionally be sodium citrate. The coating is prepared by heating a solution of the capsule material and the solute, and optionally a plasticizer. The gelling agent and hydrating agent are heated separately. When both heated solutions reach the desired temperature, they are thoroughly mixed to form the capsule, which is then hardened to the desired shape as it cools. (See also EP 0 974 345, incorporated herein by reference).

The composition may also include a bioadhesive molecule which allows adherence of the compositions to the intestinal wall. Such bioadhesives include but are not limited to those described in U.S. Pat. Nos. 5,876,744; 5,474,768;

and 4,615,697. See also Lehr et al., J. Pharm Pharmacal. 44:(1992) pp. 402–407 (incorporated herein by reference).

After the tablet is swallowed, the capsule goes through the stomach and into the upper intestine by which time the shell is dissolved and the matrix is exposed. The matrix comprising the same saw palmetto extract first becomes available to the body in the upper (small) intestine and is released in the intestine over the next 8–10 hours as the matrix traverses the small intestine releasing its extract before entry into the large intestine.

EXAMPLE 2

Formulation of Saw Palmetto Extract and Antispasmodic Compound

An additional formulation of the present invention comprises a two-part hard shell capsule that encases a matrix that in turn comprises about 50 mg to about 1 g of saw palmetto extract. Preferably, the shell comprises a material free of animal components. The dosage capsule also contained about 1 mg to about 1,000 mg of one or more antispasmodic compounds, such as extracts or tinctures of Belladonna alkaloid, Choleus forskholi, European goldenrod, peppermint, and Passion Fruit seed. The tablet is formed in the same manner described above with respect to Example 1, and allows extended release of the tablet contents during transit through the intestinal tract.

Thus, what has been described is a composition and method for treating BPH and improving the effectiveness of therapies utilizing saw palmetto extract. While the present invention has been described with respect to what are presently considered to be the preferred embodiments, it is to be understood that the invention is not limited to the disclosed embodiments. To the contrary, the invention is intended to cover various modifications and equivalent arrangements included within the spirit and scope of the appended claims. Therefore, the scope of the following claims is to be accorded the broadest interpretation so as to encompass all such modifications and equivalents.

We claim:

1. An oral composition for use in treating symptoms of benign prostatic hyperplasia, consisting essentially of:
   a therapeutically effective amount of a saw palmetto extract;
   a phytotherapeutic agent that minimizes smooth muscle contractions; and
   a controlled release system, wherein said controlled release system consists essentially of:
   a coating formed from a material impervious to acidic conditions in the stomach that is soluble in the duodenum and small intestine.

2. The composition of claim 1, wherein the controlled release system is selected from the group consisting of:
   microencapsulation in coatings of variable thickness, each with a different dissolution pattern;
   encapsulation in a material matrix that dissolves slowly in the neutral environment of the duodenum and small intestine; and
   binding bioadhesives that adhere to the wall of the small intestine.

3. The composition of claim 1, wherein the phytotherapeutic agent is selected from the group consisting of Belladonna Alkaloid, Choleus Forskholi, European Goldenrod, Peppermint, and Passion Fruit seed.

4. An oral composition for improving the effectiveness of saw palmetto extract therapy, consisting essentially of:
   a therapeutically effective amount of a saw palmetto extract;
   a therapeutically effective amount of a phytotherapeutic agent that minimizes smooth muscle contractions; and
   a controlled release system, wherein said controlled release system consists essentially of:
   a coating formed from a material impervious to acidic conditions in the stomach that is soluble in the duodenum and small intestine.

5. The composition of claim 4, wherein the controlled release system is selected from the group consisting of:
   microencapsulation in coatings of variable thickness, each with a different dissolution pattern;
   capsulation in a material matrix that dissolves slowly in the neutral environment of the duodenum and small intestine; and
   binding bioadhesives that adhere to the wall of the small intestine.

6. The composition of claim 4, wherein the phytotherapeutic agent is selected from the group consisting of Belladonna Alkaloid, Choleus Forskholi, European Goldenrod, Peppermint, and Passion Fruit seed.

7. An improved oral saw palmetto extract composition, consisting essentially of:
   a therapeutically effective amount of a saw palmetto extract;
   a therapeutically effective amount of a phytotherapeutic agent that reduces smooth muscle contractions; and
   a controlled release system, wherein said system is selected from the group consisting of:
   microencapsulation in coatings of variable thickness, each with a different dissolution pattern;
   encapsulation in a material matrix that dissolves slowly in the neutral environment of the duodenum and small intestine; and
   binding with bioadhesives that adhere to the wall of the small intestine.

8. A method of treating benign prostatic hyperplasia, comprising the step of:
   administering a therapeutically effective amount of a saw palmetto extract in combination with a therapeutically effective amount of a phytotherapeutic agent that reduces smooth muscle contractions further comprising an oral delivery vehicle comprising a coating formed from a material impervious to acidic conditions in the stomach which is soluble in the duodenum and small intestine.

9. The method of claim 8, wherein the saw palmetto extract is released into the bloodstream over an extended period.

10. The method of claim 8, wherein the oral delivery vehicle is selected from the group consisting of:
    microencapsulation in coatings of variable thickness, each with a different dissolution pattern;
    encapsulation in a material matrix that dissolves slowly in the neutral environment of the duodenum and small intestine; and
    binding bioadhesives that adhere to the wall of the small intestine.

11. The method of claim 8, wherein the coating passes through the stomach intact.

12. The method of claim 8, wherein the saw palmetto extract is initially released in the duodenum.

13. The method of claim 8, wherein the saw palmetto extract is released before it enters the colon.

14. A method of improving the efficacy of saw palmetto extract treatment, comprising the steps of:

providing a therapeutically effective amount of a saw palmetto extract;

providing a therapeutically effective amount of a phytotherapeutic agent that reduces smooth muscle contractions; and encapsulating the saw palmetto extract and the phytotherapeutic agent in a coating formed from a material impervious to acidic conditions in the stomach which is soluble in the duodenum and small intestine.

15. The method of claim 14, wherein the saw palmetto extract is released into the bloodstream over an extended period.

16. The method of claim 14, wherein the coating is selected from the group consisting of:

microencapsulation in coatings of variable thickness, each with a different dissolution pattern;

encapsulation in a material matrix that dissolves slowly in the neutral environment of the duodenum and small intestine; and binding bioadhesives that adhere to the wall of the small intestine.

17. The method of claim 14, wherein the coating passes through the stomach intact.

18. The method of claim 14, wherein the saw palmetto extract is initially released in the duodenum.

19. The method of claim 14, wherein the saw palmetto extract is released before it enters the colon.

* * * * *